United States Patent [19]

Pollak et al.

[11] Patent Number: 5,725,838
[45] Date of Patent: Mar. 10, 1998

[54] RADIOLABELED D4 RECEPTOR LIGANDS

[75] Inventors: Alfred Pollak, Toronto; Robert Dunn-Dufault, Guelph; John Thornback, Toronto, all of Canada

[73] Assignee: Resolution Pharmaceuticals, Inc., Mississauga, Canada

[21] Appl. No.: 747,311

[22] Filed: Nov. 12, 1996

Related U.S. Application Data

[63] Continuation-in-part of Ser. No. 657,784, May 31, 1996, abandoned.

[51] Int. Cl.$^6$ .................. A61K 51/00; A61M 36/14
[52] U.S. Cl. ............. 424/1.85; 424/1.81; 548/400; 544/362
[58] Field of Search .................. 424/1.11, 1.65, 424/1.81, 1.85, 9.1, 9.3, 9.4, 9.5, 9.6; 544/362, 336, 358, 359, 360, 361; 548/400

[56] References Cited

U.S. PATENT DOCUMENTS

| | | | |
|---|---|---|---|
| 3,362,956 | 1/1968 | Archer | 260/268 |
| 3,511,841 | 5/1970 | Archer | 260/268 |
| 5,219,860 | 6/1993 | Chambers et al. | 514/278 |
| 5,304,367 | 4/1994 | Biegon | 424/1.11 |
| 5,324,733 | 6/1994 | Billington et al. | 514/278 |
| 5,372,813 | 12/1994 | Mathis, Jr. et al. | 424/1.85 |
| 5,432,177 | 7/1995 | Baker et al. | 514/253 |
| 5,576,319 | 11/1996 | Baker et al. | 514/253 |
| 5,622,950 | 4/1997 | Baker et al. | 514/249 |

FOREIGN PATENT DOCUMENTS 9420497  9/1994  WIPO.

OTHER PUBLICATIONS

Molecular Pharmacology; vol. 50, No. 6, 1996, pp. 1658–1664, S. Patel et al., "Identification and characterization of [1251] L750,667, a novel . . . ". (Dec. 1996).

Patel et al (Dec. 1996). Molecular Pharmacology, vol. 50, pp. 1658–1664, "Identification and Pharmacological Characterization of [$^{125}$I] L–750,667, a Novel Radioligand for the Dopamine $D_4$ Receptor".

Chavez–Eng (Mar. 1997), Journal of Chromatography B, vol. 691, pp. 77–85, "Picogram Determination of a Novel Dopamine $D_4$ Receptor Antagonist in Human Plasma and Urine by Liquid Chromatogy with Atmospheric Pressure Chemical Ionization Tanden Mass Spectrometry".

Kung et al (Nov. 29, 1996), Life Sciences, vol. 60, No. 2, pp. 91–100, "Characterization of a Novel Iodinated Ligand, IPMPP, for Human Dopamine $D_4$ Receptors Expressed in Cho. Cells".

Kulagowski et al J Med Chem, 1996, 39:1941 "3–[ [4–4–(Chlorophenyl)piperazin–1–yl]methyl]–1H–pyrrolo [2,3–b]pyridine: An Antagonist with High Affinity and Selectivity for the Human Dopamine D4 Receptor".

Kung et al Society for Neurosciences Abstracts, vol. 22, Part 2, Abstract No. 330.5, p. 828, presented at the 26th Annual Meeting of the Society for Neurosciences, Nov. 16–21, 1996, Washington, D.C.

"Binding Characteristics of Iodinated Ligands for Dopamine D4 Receptors".

Primary Examiner—John Kight
Assistant Examiner—Dameron Jones
Attorney, Agent, or Firm—Nikaido, Marmelstein, Murray & Oram LLP

[57] ABSTRACT

Herein described are radiolabeled compounds and their precursors useful to image D4 receptors in vivo, of the formula:

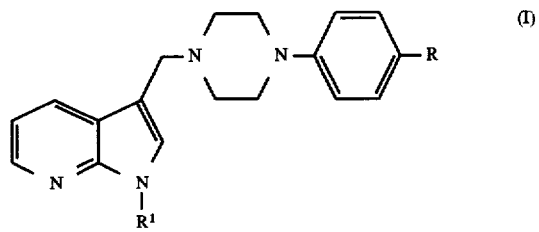

(I)

wherein R is selected from iodo, tri(loweralkyl)tin and a radioisotopically labeled iodide and $R^1$ is selected from H and alkoxycarbonyl, with the proviso that R is not iodo when $R^1$ is H.

The radiopharmaceutical compounds are useful particularly to image localization of D4 receptor in the human brain, and can therefore aid in the diagnosis of schizophrenia and other medical conditions in which the D4 receptor is implicated.

21 Claims, No Drawings

RADIOLABELED D4 RECEPTOR LIGANDS

CROSS REFERENCE TO RELATED APPLICATION

This application is a continuation-in-part of application Ser. No. 08/657,784, now abandoned filed May 31, 1996.

This invention is in the field of medical diagnostics, and relates to radiolabeled compounds useful to image D4 receptor loci in brain tissue.

BACKGROUND TO THE INVENTION

Neuronal cell receptors that bind the neurotransmitter dopamine constitute a group of at least five structurally distinct proteins that can now be produced using recombinant DNA techniques. These techniques have been applied to construct cell lines that incorporate the dopamine receptor in their membranes, to provide regenerable and homogeneous substrates with which chemical libraries can be screened to identify potential CNS-active drugs.

Recent evidence strongly implicates the dopamine receptor classified as D4 in the etiology of schizophrenia. It has been suggested that compounds capable of interfering with the function of this receptor, which is present in schizophrenics at levels that are six times normal, would be useful in the treatment of this disease (Seeman et at, Nature, 1993, 365:441). Therefore, it would be desirable to provide compounds that exhibit a high degree of affinity for the D4 receptor.

Some dopamine receptor ligands currently sold as pharmaceuticals exhibit the desired affinity and antagonism for the D4 receptor, yet interact non-selectively with related dopamine receptors, particularly the D2 receptor type, which results in significant side effects that include altered motor function and tachycardia. In the context of medical diagnostics, this non-selective binding at the D4 receptor prevents the generation of an accurate image of the localization and prevalence specifically of the D4 type of dopamine receptor. It would therefore be desirable to provide compounds that, in their radiolabeled state, bind at the D4 receptor with affinity and selectivity appropriate for diagnostic imaging purposes. When used in combination with such diagnostic imaging techniques as single photon emission tomography (SPECT), such radiolabeled compounds would be useful particularly to diagnose schizophrenia and other medical conditions associated with D4 receptor anomalies.

SUMMARY OF THE INVENTION

According to one aspect of the present invention, there are provided compounds of Formula (I):

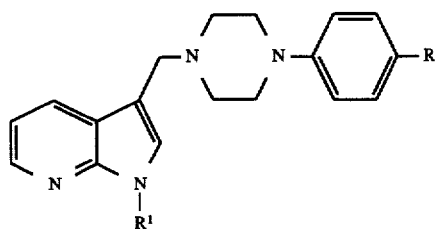

wherein R is selected from iodo, tri(loweralkyl)tin and a radioisotopically labeled iodide and $R^1$ is selected from H and alkoxycarbonyl, with the proviso that R is not iodo when $R^1$ is H.

According to another aspect of the invention, there is provided a process for preparing compounds of Formula I, wherein R is a radioisotopic iodide and $R^1$ is H, comprising the step of treating a compound of Formula I, wherein R is tri(loweralkyl)tin with a radioisotopically labelled iodide source in the presence of an oxidizing agent and an acid.

According to another aspect of the invention, there is provided another process for preparing compounds of Formula I, wherein R is a radioisotopic iodide and $R^1$ is H, comprising the steps of treating a compound of Formula I, wherein R is tri(loweralkyl)tin and $R^1$ is alkoxycarbonyl with a radioisotopically labeled iodide source in the presence of an oxidizing agent and an acid, followed by removal of the alkoxycarbonyl protecting group under acidic deprotection conditions in the same reaction vessel.

According to another aspect of the invention, there is provided a radiopharmaceutical composition comprising a compound of Formula I wherein R is a radioisotopic iodide and $R^1$ is H and a pharmaceutically acceptable carrier, such as physiological buffered saline.

In a further aspect of the invention, there is provided a method for imaging D4 receptors in vivo, comprising the step of administering systemically to a patient an effective amount of the radiopharmaceutical composition, and then imaging the composition following its accumulation at D4 receptor sites in the brain.

DETAILED DESCRIPTION OF THE INVENTION

The term lower alkyl as used herein means straight chain alkyl radicals containing from one to six carbon atoms and branched chain alkyl radicals containing three to six carbon atoms and includes methyl, n-butyl, 1-methylethyl and the like.

The term alkoxycarbonyl as used herein means straight and branched chain alkyl carbonates containing from two to six carbon atoms and includes methoxycarbonyl, ethoxycarbonyl and t-butoxycarbonyl and the like.

Compounds of the present invention are those of Formula I in which R and $R^1$ are as defined above. In embodiments of the invention R is tri(loweralkyl)tin. In a preferred embodiment, R is tributyltin or trimethyltin.

In another embodiment of the invention R is a radioisotopic iodide including $^{123}$I, $^{125}$I and $^{131}$I. In a preferred embodiment, R is $^{123}$I.

In an embodiment of the invention, $R^1$ is selected from H and alkoxycarbonyl. In a preferred embodiment, $R^1$ is selected from H and t-butoxycarbonyl. In a more preferred embodiment, $R^1$ is t-butoxycarbonyl.

Compounds of Formula I, wherein $R^1$ is H and R is a radioisotopically labeled iodide, can be prepared by reacting compounds of Formula I, wherein R is tri(loweralkyl)tin and $R^1$ is H, with radioisotopic iodide source, for example a solution of radioisotopically labeled sodium iodide (e.g. as a solution in 1N NaOH), in the presence of an acid and an oxidizing agent in an alcoholic solvent. Preferred conditions are hydrogen peroxide and hydrochloric acid in ethanol.

In a preferred method, compounds of Formula I, wherein $R^1$ is H and R is a radioisotopically labeled iodide, are prepared by reacting a compound of Formula I, wherein wherein R is tri(loweralkyl)tin and $R^1$ is alkoxycarbonyl, with a radioisotopic iodide source as described above, followed by removal of the alkoxycarbonyl protecting group under acidic conditions in the same reaction vessel. The preferred acid is hydrochloric acid.

To generate compounds of Formula I wherein $R^1$ is H and R is tri(loweralkyl)tin, an appropriately substituted piperazine derivative is coupled with the 1H-pyrrolo[2,3-b]

pyridine in the presence of formaldehyde in an aqueous buffer solution, for example, aqueous sodium acetate and acetic acetate. The 1H-pyrrolo[2,3-b]pyridine is commercially available and the piperazines are either commercially available or can be prepared by methods known to one skilled in the art. Thus 1-[4-(triloweralkyltin)phenyl]-piperazines can be prepared from 1-(4-iodophenyl)-piperazine by reaction with hexa(loweralkyl)ditin reagents under standard palladium-catalyzed cross coupling conditions, for example, in the presence of a catalytic amount of tetrakis(triphenylphosphine)palladium (0) in an inert solvent such as 1,2-dimethoxyethane at temperatures ranging from 50°–100° C., preferably at about 85° C. The 1-(4-iodophenyl)-piperazine can be prepared from 1-phenylpiperazine by reaction with an electrophilic iodine reagent under acidic aqueous conditions, for example, by treating 1-phenylpiperazine with iodine monochloride in acetic acid/water (3:1) according to Hanson et al. J. Heterocyclic Chem., 1985, 22:47.

Compounds of Formula I wherein $R^1$ is alkoxycarbonyl and R is iodo or tri(loweralkyl)tin, can be prepared by reacting compounds of Formula I wherein $R^1$ is H and R is iodo or tri(loweralkyl)tin with dialkoxydicarbonate reagents in the presence of a base in an inert solvent at temperatures in the range of 0° C. to 50° C., preferably at around room temperature. Suitable bases include sodium or potassium hydroxide or triethylamine. Suitable inert solvents include chloroform, dichloromethane or acetonitrile. Preferred conditions are potassium hydroxide in dichloromethane. The dialkoxydicarbonate compounds are readily available protecting group reagents.

Compounds of Formula I wherein $R^1$ is alkoxycarbonyl and R is tri(loweralkyl)tin, can also be prepared by reacting compounds of Formula I wherein R is iodo and $R^1$ is alkoxycarbonyl with hexa(loweralkyl)ditin reagents under standard palladium-catalyzed cross coupling conditions as described above.

In preferred embodiments of the invention, the compounds are selected from

3-[4-(4-$^{123}$I-phenyl)piperazin-1-yl]methyl-1H-pyrrolo[2,3-b]pyridine;

3-[4-(4-$^{125}$I-phenyl)piperazin-1-yl]methyl-1H-pyrrolo[2,3-b]pyridine;

3-[4-(4-$^{131}$I-phenyl)piperazin-1-yl]methyl-1H-pyrrolo[2,3-b]pyridine;

3-{4-[4-(tributyltin)phenyl]piperazin-1-yl }methyl-1H-pyrrolo[2,3-b]pyridine;

3-[4-(4-iodophenyl)piperazin-1-yl]methyl-1-(t-butoxycarbonyl)-pyrrolo[2,3-b]pyridine;

3-{4-[4-(trimethyltin)phenyl]piperazin-1-yl}methyl-1-(t-butoxycarbonyl)-pyrrolo[2,3-b]pyridine; and 3-{4-[4-(trimethyltin)phenyl]piperazin-1-yl}methyl-1H-pyrrolo[2,3-b]pyridine.

In more preferred embodiments of the invention, the compounds are selected from

3-[4-(4-$^{123}$I-phenyl)piperazin-1-yl]methyl-1H-pyrrolo[2,3-b]pyridine;

3-{4-[4-(tributyltin)phenyl]piperazin-1-yl}methyl-1H-pyrrolo[2,3-b]pyridine;

3-[4-(4-iodophenyl)piperazin-1-yl]methyl-1-(t-butoxycarbonyl)-pyrrolo[2,3-b]pyridine;

3-{4-[4-(trimethyltin)phenyl]piperazin-1-yl}methyl-1-(t-butoxycarbonyl)-pyrrolo [2,3-b]pyridine; and 3-{4-[4-(trimethyltin)phenyl]piperazin-1-yl}methyl-1H-pyrrolo[2,3-b]pyridine.

The compounds of the invention wherein R is a radioisotopic iodide are formulated as radiopharmaceutical compositions together with any physiologically and radiologically tolerable vehicle appropriate for administering the compound systemically. Included among such vehicles are phosphate buffered saline solutions, buffered for example to pH 7.4.

It is contemplated that the present compounds will be administered to patients by intravenous injection or infusion at doses suitable (e.g. between 1 and 10 mCi) to generate an image of the compound as localized within the brain, using for example a gamma camera. It is further contemplated that the method of the present invention can usefully be applied diagnose to patients suspected of suffering from schizophrenia. For these patients, diagnosis can be aided or confirmed by determining the intensity of radiolabeled compound relative to the brain of a healthy patient; greater image intensity is indicative of an overabundance of D4 receptor, and is hence indicative of a schizophrenic condition.

EXAMPLE 1

Prepartion of 1-(4-iodophenyl)piperazine

The title compound was prepared by adding a suspension of iodine monochloride (1.2 g, 7.4 mmol) in acetic acid/water (3:1, 7 ml) to a solution of 1-phenylpiperazine (1.09 g, 6.7 mmol) in acetic acid/water (3:1, 5 ml) at 50° C. The reaction was stirred and heated at 55° C. for 1 hour, then at room temperature for 1 hour. The solution was poured into 100 mL of crushed ice and the pH adjusted to 13 with 4N NaOH. The product was then extracted into dichloromethane (2×100 mL) and the combined organic layers were dried over sodium sulfate, filtered and concentrated to provide the title compound as a pale yellow solid (1.4 g, 72.5%).

EXAMPLE 2

Preparation of 1-[4-(triloweralkyltin)phenyl]piperazines

To a solution of 1-(4-iodophenyl)piperazine (50 mg, 0.174 mmol, 1 eq) and hexa(loweralkyl)ditin (0.208 mmol, 1.2 eq) in 1,2-dimethoxyethane (7.5 mL) under argon was added tetrakis(triphenylphosphine)palladium(0) (0.1 eq). The reaction was refluxed for 4–8 hours followed by filtration through celite and washing with methanol (10 mL). The organic layer was concentrated and the corresponding products were purified by preparative thin layer chromatography on silica gel using dichloromethane/methanol/aqueous ammonium hydroxide (50:7:1) as eluent to provide the title compounds as white solids.

Using the above procedure the following compound was prepared:

(a) 1-[4-(Tributyltin)phenyl]piperazine, from hexa-(n-butyl)ditin.

EXAMPLE 3

Preparation of 3-[4-(4- substituted-phenyl)piperazin-1-yl] methyl-1H-pyrrolo[2,3-b]pyridines A solution of 1-[4-(substituted)phenyl]piperazine (0.25 mmol, 1 eq), formaldehyde (0.3 mmol, 1.2 eq) and sodium acetate (0.25 mmol, 1 eq) in acetic acid/water (300 μL, 2:1) was allowed to stir at room temperature for 10 minutes then 1H-pyrrolo[2,3-b]pyridine (0.25 mmol, 1 eq) was added and the solution stirred overnight. Ammonium hydroxide (aq, 30%, 1 mL) was then added and the product extracted into ethyl acetate. The organic layer was dried over sodium sulfate and concentrated. The corresponding product was purified by preparative thin layer chromatography on silica gel using dichloromethane/methanol/aqueous ammonium hydroxide (50:7:1) as eluent.

Using the above procedure the following compound was prepared:

a) 3-[4-(4-iodophenyl)-piperazin-1-yl]methyl-1H-pyrrolo[2,3-b]pyridine, from 1-(4-iodophenyl)piperazine (Example 1), yellow solid (51 mg, 49%).

EXAMPLE 4

Synthesis of 3-[4-(4-iodophenyl)piperazin-1-yl]methyl-1-(t-butoxycarbonyl)pyrrolo[2,3-b]pyridine To 3-[4-(4-iodophenyl)piperazin-1-yl]methyl-1H-pyrrolo[2,3-b]pyridine (Example 3a, 0.5 mmol, 209 mg) in dichloromethane (5 mL) under argon was added powdered KOH (1.0 mmol, 56 mg), followed by di-t-butyl dicarbonate (0.55 mmol, 120 mg). The reaction was stirred for 1 hour at room temperature. The solution was filtered and concentrated to a yellow oily solid. The product was purified by flash chromatography on silica gel using 30 to 50% ethyl acetate in hexanes (with 1% triethylamine) as eluent. The pooled fractions were concentrated to yield the title compound as a white solid (190 mg, 73%). $MH^+$519.40.

EXAMPLE 5

Synthesis of 3-{4-[4-(trimethyltin)phenyl]piperazin-1-yl}methyl-1-(t-butoxycarbonyl)pyrrolo[2,3-b]pyridine To 3-[4-(4-iodophenyl)piperazin-1-yl]methyl-1-(t-butoxycarbonyl)pyrrolo[2,3-b]pyridine (Example 4, 0.10 mmol, 52 mg) and hexamethylditin (0.105 mmol, 34.5 mg) in dry dimethoxyethane (3 mL) under argon was added tetrakis(triphenylphosphine)palladium (0) (0.010 mmol, 12 mg). The reaction was fitted with a condenser and heated at 60° C. for 1 hour. The solution was cooled to room temperature, filtered through a short silica gel bed and washed with ethyl acetate. The product was concentrated and purified on a preparative silica chromatography plate developed with 50% ethyl acetate in hexanes with 1% TEA to yield the title compound as a pale yellow oil (30 mg, 54%). $MH^{+calc}$ 555.38, found 555.44.

EXAMPLE 6

Preparation of 3-{4-[4-(radioisotopic-iodo)phenyl]piperazin-1-yl}methyl-1H-pyrrolo[2,3-b]pyridine Method A:

A solution of the 3-{4-[4-(triloweralkyltin)phenyl]piperazin-1-yl}methyl-1H-pyrrolo[2,3-b]pyridine (50–200 µg) in dichloromethane (300 µL) is concentrated to an oil by passing argon over the solution through a septa in a 2 mL vial. Ethanol (300 µL) is then added and the resulting solution swirled to ensure complete dissolution. A solution of radioisotopically labeled sodium iodide (6 µL in 0.1N NaOH) in ethanol (300 µL) is prepared in a reactivial and to this is added sequentially, the solution of 3-{4-[4-(triloweralkyltin)phenyl]-piperazin-1-yl}methyl-1H-pyrrolo[2,3-b]pyridine, hydrochloric acid (0.3N, 17 µL) and hydrogen peroxide (3%, 100 µL). The resulting solution is swirled, adequately shielded and left stoppered for 15 minutes at room temperature. After venting in the fumehood, aqueous solutions of sodium metabisulfite (150 mg/mL, 100 µL), sodium carbonate (saturated, 60 µL) and saline (100 µL) are added and the product extracted into dichloromethane (300 µL). The organic later is separated and analysed and purified by HPLC.

Method B:

A solution of 3-{4-[4-(triloweralkyltin)phenyl]piperazin-1-yl}methyl-1-(alkoxycarbonyl)-pyrrolo[2,3-b]pyridine (200 ug) was dissolved in ethanol (100 uL). To the $Na^{123}I$ solution (2 mCi, in 0.1N NaOH) in a 3 mL reactivial was added ethanol (200 uL). Sequentially added were hydrochloric acid (1N, 100 uL), the solution of 3-{4-[4-(triloweralkyltin)phenyl]-piperzin-1-yl}methyl-1-(alkoxycarbonyl)-pyrrolo[2,3-b]pyradine and hydrogen peroxide (3%, fresh, 100 uL). The vial was swirled, adequately shielded, and left to react stoppered for 15 minutes at room temperature. The iodination reaction was complete after 15 minutes, however, the protecting group hydrolysis required an hour to finish. The septum was then vented in the fumehood and sodium metabisulfite (150 mg/mL, 100 uL), sodium carbonate (sat, 200 uL) and saline (100 uL) were added. The product was extracted into dichloromethane (300 uL) which was removed carefully by syringe. The organic layer contained the desired product. HPLC analysis was used to confirm the results by comparing the product retention time to that of the authentic cold product as well as the starting material and intermediate.

Using Method B, the following compound was prepared: 3-[4-(4-$^{123}$I-phenyl)piperazin-1-yl]methyl-1H-pyrrolo[2,3-b]pyridine, from 3-{4-[4-(trimethyltin)phenyl]piperazin-1-yl}methyl-1-(t-butoxycarbonyl)pyrrolo[2,3-b]pyridine (Example 5).

EXAMPLE 7

Receptor Binding Affinities

D2 and D4 receptor-binding affinities of the compounds of Example 3 were evaluated as described in WO95/17400 (incorporated herein by reference) for their ability to reduce binding of $^3$H-spiperone as compared to the reference compound clozapine. The potency of the test compound to reduce $^3$H-spiperone binding directly correlated to its binding affinity for the receptor.

Briefly, the D4 receptor was utilized in the form of membrane preparations obtained from HEK 298 cells stably transfected with human D4 receptor (D4.2 sub-type). D2 receptor was utilized in the form of membrane preparations obtained from $GH_4C_1$ (rat pituitary) cells stably transfected with the human D2 receptor (short isoform). The total spiperone binding assay was started by the addition of 500 µl (50 µg protein) membrane homogenate to a solution of 900 µl incubation buffer and 100 µl (0.25 nM final conc.) $^3$H-spiperone. The binding reaction was stopped and the samples were filtered under vacuum and filters were then washed 3 times with 5 ml ice cold 50 mM Tris buffer (pH 7.4). Individual filter disks were put in scintillation vials (Biovials, Bechman). Ready Protein Plus liquid scintillant (5 ml, Beckman) was added and the vials counted by liquid scintillation spectrophotometry (Beckman LSC 6500) after equilibrating for three hours at room temperature to determine total binding ($B_r$).

Non-specific binding for D4 was assayed by incubating membrane homogenate, $^3$H-spiperone and fresh dopamine. Filtrate was counted using the same procedure as in the total binding assay described above to give the non-specific binding value (NSB). Non-specific binding for D2 was similarly assessed, with the exception that (-)-sulpiride was used in place of dopamine.

To assess displacement, membrane homogenate was incubated with $^3$H-spiperone and test compound dissolved in DMSO. Filtrate was counted using the same procedure as in the total binding assay described above, to give the displacement binding value ($B_D$).

The test compounds were initially assayed at 1 and 0.1 µM and then at a range of concentrations chosen such that the middle dose would cause about 50% inhibition of $^3$H-spiperone binding. Specific binding in the absence of test compound ($B_0$) was the difference of total binding ($B_r$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of % $B/B_0$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions.

Assay results (Ki) are reported in the following Table, and show clearly the D4 selectivity of compounds of the invention:

| Compound | D4 (nM) | D2 (nM) |
|---|---|---|
| 3-[4-(4-iodophenyl)-piperazin-1-yl]methyl-1H-pyrrolo[2,3-b]pyridine | 0.16 | 2366 |

We claim:
1. A compound of Formula (I):

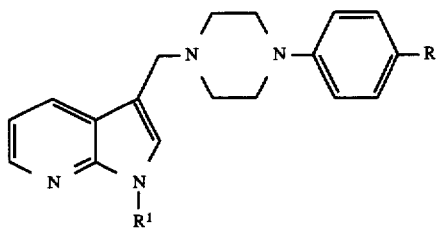

wherein R is selected from iodo, tri(loweralkyl)tin and a radioisotopically labeled iodide and $R^1$ is selected from H and alkoxycarbonyl, with the proviso that R is not iodo when $R^1$ is H.

2. A compound according to claim 1, wherein R is tri(loweralkyl)tin.

3. A compound according to claim 2, wherein R is selected from tributyltin and trimethyltin.

4. A compound according to claim 1, wherein $R^1$ is H.

5. A compound according to claim 1, wherein $R^1$ is t-butoxycarbonyl.

6. A compound according to claim 4, wherein $R^1$ is t-butoxycarbonyl.

7. A compound according to claim 4, wherein R is radioisotopically labeled iodide.

8. A compound according to claim 7, wherein R is $^{123}$I.

9. A compound according to claim 1 selected from:
3-[4-(4-$^{123}$I-phenyl)piperazin-1-yl]methyl-1H-pyrrolo[2,3-b]pyridine;
3-[4-(4-$^{125}$I-phenyl)piperazin-1-yl]methyl-1H-pyrrolo[2,3-b]pyridine;
3-[4-(4-$^{131}$I-phenyl)piperazin-1-yl]methyl-1H-pyrrolo[2,3-b]pyridine;
3-{4-[4-(tributyltin)phenyl]piperazin-1-yl }methyl-1-1H-pyrrolo[2,3-b]pyridine;
3-[4-(4-iodophenyl)piperazin-1-yl]methyl-1-(t-butoxycarbonyl)-pyrrolo[2,3-b]pyridine;
3-{4-[4-(trimethyltin)phenyl]piperazin-1-yl }methyl-1-(t-butoxycarbonyl) -pyrrolo[2,3-b]pyridine; and
3-{4-[4-(trimethyltin)phenyl]piperazin-1-yl }methyl-1H-pyrrolo[2,3-b]pyridine.

10. A compound according to claim 9 selected from:
3-[4-(4iodophenyl)piperazin-1-yl]methyl-1-(t-butoxycarbonyl)-pyrrolo[2,3-b]pyridine; and
3-{4-[4-(trimethyltin)phenyl]piperazin-1-yl }methyl-1-(t-butoxycarbonyl)-pyrrolo[2,3-b]pyridine.

11. A process for preparing a compound of Formula I as defined in claim 1 wherein R is a radioisotopic iodide and $R^1$ is H, comprising the step of removing the protecting group on the indole nitrogen of a compound of Formula I, wherein R is a radioisotopic iodide and $R^1$ is alkoxycarbonyl, by reaction with an acid.

12. A process for preparing a compound of Formula I as defined in claim 1 wherein R is a radioisotopic iodide and $R^1$ is alkoxycarbonyl, comprising the step of reacting a compound of Formula I, wherein R tri(loweralkyl)tin and $R^1$ is alkoxycarbonyl with a source of radioisotopically labeled iodide in the presence of an oxidizing agent and acid.

13. A process for preparing a compound of Formula I as defined in claim 1 wherein R is a radioisotopic iodide and $R^1$ is H, comprising the treatment of compound of Formula I, wherein R is tri(loweralkyl)tin and $R^1$ is alkoxycarbonyl, with a radioisotopically labeled iodide source, an oxidizing agent and an acid so that removal of the alkoxycarbonyl group on the indole nitrogen and addition of the radioisotopic iodide is accomplished in the same reaction vessel.

14. A process for preparing a compound of Formula I as defined in claim 1 wherein R is a radioisotopic iodide and $R^1$ is H, comprising the step of reacting a 3-{4-[4-(triloweralkyltin)phenyl]-piperazin-1H-pyrrolo[2,3-b] pyridine with a radioisotopically labeled iodide source in the presence of an oxidizing agent and acid.

15. A process, comprising the step of reacting hexa (loweralkyl)ditin reagents under standard palladium-catalyzed cross-coupling conditions with:
(a) a compound of Formula I as defined in claim 1 wherein R is iodo and $R^1$ is alkoxycarbonyl to prepare a compound of Formula I wherein R is tri(loweralkyl) tin and $R^1$ is alkoxycarbonyl; or
(b) 3-[4-(4-iodophenyl)piperazin-1-yl]methyl-1H-pyrrolo [2,3-b]pyridine to prepare a compound of Formula I wherein R is tri(loweralkyl)tin and $R^1$ is H.

16. A process for preparing a compound of Formula I as defined in claim 1 wherein R is iodo or tri(loweralkyl)tin and $R^1$ is alkoxycarbonyl, comprising the step of treating a compound of Formula I, wherein R is iodo or tri(loweralkyl) tin and $R^1$ is H, with a dialkoxydicarbonate reagent in the presence of a base.

17. A process for preparing a compound of Formula I as defined in claim 1 wherein R is tri(loweralkyl)tin and $R^1$ is H, comprising the step of coupling a 1-[4-(triloweralkyltin) phenyl]piperazine with 1H-pyrrolo[2,3-b]pyridine in the presence of formaldehyde in an aqueous buffer solution.

18. A radiopharmaceutical composition, comprising a radiopharmaceutically acceptable carrier and a compound as defined in claim 7 in an amount effective to image a human brain.

19. A radiopharmaceutical composition, comprising a radiopharmaceutically acceptable carrier and a compound as defined in claim 8 in an amount effective to image a human brain.

20. A method of radioimaging a human brain, comprising the step of administering systemically to a patient a radiopharmaceutical composition as defined in claim 18.

21. A method of radioimaging a human brain, comprising the step of administering systemically to a patient a radiopharmaceutical composition as defined in claim 19.

* * * * *